United States Patent [19]

Sellegaard

[11] Patent Number: 4,710,394

[45] Date of Patent: Dec. 1, 1987

[54] PREPARATION AND PROCESS FOR THE PRESERVATION OF PLANTS

[76] Inventor: Eric L. Sellegaard, 8 Domaine du Camp Lauvas -1575 Rte de Valbonne, 06520 Mougins, France

[21] Appl. No.: 891,119

[22] Filed: Jul. 28, 1986

[30] Foreign Application Priority Data

Aug. 2, 1985 [FR] France ................... 85 11992

[51] Int. Cl.$^4$ .............. C09K 15/32; A01G 5/06; B05D 1/18
[52] U.S. Cl. .......................... 427/4; 8/495; 252/400.1; 252/400.2; 252/400.53; 252/400.61; 252/400.62; 427/439; 428/22
[58] Field of Search .......... 427/4, 439; 428/22; 252/400.1, 400.2, 400.53, 400.61, 400.62; 8/495

[56] References Cited

U.S. PATENT DOCUMENTS

| | | | |
|---|---|---|---|
| 2,978,348 | 4/1961 | Fessenden ................. | 427/4 |
| 4,243,693 | 1/1981 | Nordh ..................... | 427/4 |
| 4,248,734 | 2/1981 | Romero-Sierra ............ | 427/4 X |
| 4,349,580 | 9/1982 | Romero-Sierra ............ | 427/4 |

*Primary Examiner*—Michael R. Lusignan
*Attorney, Agent, or Firm*—Erwin S. Teltscher

[57] ABSTRACT

This invention relates to a dry preparation containing essentially 1–6% by weight of citric acid, 30–60% by weight of a dye and 40–60% by weight of an inorganic salt. Said preparation may be used in solution to preserve plants.

9 Claims, No Drawings

PREPARATION AND PROCESS FOR THE PRESERVATION OF PLANTS

BACKGROUND OF THE INVENTION

The present invention relates to a preparation and a method enabling plants to preserve their fresh appearance for a long period of time, even after having been extracted from their natural environment.

The term plants includes herein plants, flowers, bushes and trees, as well as parts thereof, with the understanding that the preparation and the process for the preservation may vary according to the type of plant.

It has suprisingly been found that the natural appearance and strength of plants and parts thereof can be maintained for a very long time (one year or more) by immersing the roots or the freshly cut stem in a solution which contains, besides water and glycerol, one or more dyes, one or more inorganic salts and an organic acid, preferably citric acid.

Furthermore it has been found that the preservation, particularly of parts of conifers, can be improved considerably by an additional treatment with ethanol or methanol.

SUMMARY OF THE INVENTION

The invention pertains firstly to a dry preparation, intended to be used in dissolved form for the preservation of plants and parts thereof, which preparation contains one or more inorganic salts, one or more dyes and 1-6% by weight of an organic acid.

Generally the inorganic salts are water soluble, but water insoluble salts, which dissolve in the presence of the organic acid, are also suitable. Examples of such salts are calcium and magnesium carbonate.

The dry preparation according to the invention contains as inorganic salts preferably salts constituted of the cations potassium, sodium, calcium, magnesium and/or manganese and the anions nitrate, chloride, sulfate, carbonate and/or phosphate. The inorganic salts preferably comprise salts which can be considered as nutrients for plants, particularly potassium nitrate. The latter salt preferably constitutes 20-100% by weight of the inorganic salts. Preferably, the inorganic salts are present in an amount of 40-60% by weight of the dry preparation.

The dyes can be usual organic dye-stuffs, such as tartrazine yellow, quinoline yellow, sunset yellow, para-orange, amaranth red, ponceau red, erythrosine, patent blue and food green or mixtures thereof. Preferably, the dyes are chosen in such a way, that a discoloration, for example of chlorophyll, which might occur during the preservation, is made up for. Alternatively, the dyes can be chosen to bring about special effects, for example to produce a blue shade on branches of fir or to provide plants with a colour differing from their natural colour. Preference is given to a mixture of tartrazine and food green, which dyes are registered and known, respectively, in the United States of America under the names F, D & C Yellow Nr. 5, CI 19140 and F, D & C Green Nr. 3, CI 42053. The dyes are present in an amount of 30-60% by weight and, preferably, from 38-55% by weight of the preparation.

Preferably, the organic acid has the form of a powder and in particular it is citric acid. An adequate grade of citric acid is commercially available as monohydrate with the name R.P. Normaque 99,7%. Citric acid constitutes 1-6% by weight and preferably 1.8-5% by weight of the dry preparation.

The inorganic salts, dyes and organic acid are mixed in a proportion appropriate for the particular purpose to form a homogeneous, dry composition.

DESCRIPTION OF THE PREFERRED EMBODIMENTS

The components of preferred dry preparations, as well as the components of a particularly preferred preparation (A) are mentioned below in percent by weight.

|  |  | A |
| --- | --- | --- |
| potassium nitrate | 40-50 | 44 |
| sodium sulfate | 3-7 | 5 |
| mixed calcium and magnesium carbonate with 12% by weight Mg | 8-12 | 10 |
| citric acid | 1.8-2.2 | 2 |
| tartrazine, F, D & C Yellow Nr. 5 | 12-18 | 15 |
| food green, F, D & C Green No. 3 | 22-26 | 24 |

Other examples of dry preparations are listed in the table.

The dry preparation can be stored and at a desired moment it can be dissolved, preferably in a mixture of water and glycerol, in order to be used for the preservation of plants and/or parts thereof.

The mixture of water and glycerol preferably contains 25-45% by volume glycerol and 75-55% by volume water. The dry preparation is dissolved in the mixture of water and glycerol in a proportion of 1-3% by weight, preferably about 2.5% by weight.

The preservation of plants and parts thereof is achieved by dipping the roots or the freshly cut stem into the liquid preparation, for example for 20 hours to 10 days, preferably at a temperature between ambient temperature and 45° C. and at a relative humidity of not more 60%, and subsequently allowing the plant or the part thereof to dry with the roots or the stem in an upright position, in a warm and dry atmosphere.

For the preservation of cut flowers for example, the stems can be held in a 2.5% by weight solution of preparation A in water/glycerol (70/30) at 22° C. for 20-30 hours, followed by drying the flowers with their heads down for about 7 days.

The same preparation A can for example be used for preserving the fresh appearance of cypress and juniper type plants at 37° C., before drying for 1-10 days.

For the preservation of conifers, such as pine, fir and spruce, or parts thereof, advantageously a liquid preparation containing 1-2.5% by volume methanol or ethanol is used. The treatment in such a preserving solution can for example be carried out at 45° C.

The preservation of conifers is particularly important, as this type of tree is frequently used for decorative purposes, particularly as christmas tree. The invention provides a means to prevent loss of needles and to keep the trees in a fresh condition for a long period of time.

Citric acid added according to the invention performs various functions. It acts as a growth stimulator and has a stabilizing effect on the powder mixture of nutrients and dyes. Furthermore, it appears that the presence of citric acid allows the treatment temperature to be raised to about 45° C. without any adverse effect. As a consequence of the increased temperature, the viscosity of glycerol in the liquid preparation diminishes, thus facilitating, accelerating and improving the action of the preparation. The amount of glycerol can then be increased to about 40% which is advantageous for the preservation.

Finally it is found that the presence of citric acid provides the plants with a natural colour, the addition of toxic chemicals, like silver nitrate, being not necessary, which addition is legally forbidden in many countries.

The ultimate result of following the method of the invention is that flowers and plants are obtained which feel soft and flexible, do not look desiccated and, even with shaking, show no tendency to disintegrate. Thus, genuine and durable plants, without any fragility, are provided.

In the table below some examples are given of dry compositions of the invention, wherein the numbers refer to percent by weight.

TABLE

| Components | Composition | | | | |
|---|---|---|---|---|---|
| | 1 | 2 | 3 | 4 | 5 |
| Tartrazine | 28 | 28 | 36 | 0 | 16 |
| patent blue | 2 | 4 | 2 | 1 | 9 |
| food green | 20 | 4 | 0 | 0 | 16 |
| amaranth | 0 | 0 | 0 | 20 | 0 |
| para-orange | 0 | 0 | 0 | 0 | 0 |
| quinoline yellow | 0 | 14 | 12 | 0 | 0 |
| erythrosine | 0 | 0 | 0 | 29 | 0 |
| potassium nitrate | 34 | 34 | 34 | 34 | 40 |
| sodium sulfate | 4 | 4 | 4 | 4 | 5 |
| mixed Ca Mg carbonate | 8 | 8 | 8 | 8 | 9 |
| citric acid | 4 | 4 | 4 | 4 | 5 |

| Components | Composition | | | | | | | | |
|---|---|---|---|---|---|---|---|---|---|
| | 6 | 7 | 8 | 9 | 10 | 11 | 12 | 13 | 14 |
| Tartrazine | 34 | 26 | 36 | 36 | 0 | 20 | 0 | 50 | 0 |
| patent blue | 2 | 2 | 2 | 0 | 0 | 2 | 0 | 0 | 0 |
| food green | 14 | 8 | 0 | 4 | 0 | 28 | 0 | 0 | 0 |
| amaranth red super | 0 | 0 | 0 | 0 | 50 | 0 | 0 | 0 | 0 |
| quinoline yellow | 0 | 14 | 12 | 10 | 0 | 0 | 0 | 0 | 0 |
| sunset yellow 85% | 0 | 0 | 0 | 0 | 0 | 0 | 0 | 0 | 50 |
| Ponceau 4R 85% | 0 | 0 | 0 | 0 | 0 | 0 | 50 | 0 | 0 |
| potassium nitrate | 30 | 30 | 30 | 30 | 30 | 30 | 30 | 30 | 30 |
| sodium sulfate | 4 | 4 | 4 | 4 | 4 | 4 | 4 | 4 | 4 |
| manganese sulfate monohydrate | 8 | 8 | 8 | 8 | 8 | 8 | 8 | 8 | 8 |
| calcium hydrogen phosphate | 4 | 4 | 4 | 4 | 4 | 4 | 4 | 4 | 4 |
| citric acid | 4 | 4 | 4 | 4 | 4 | 4 | 4 | 4 | 4 |

500 g of one of these compositions is mixed with 14 liter of water and 6 liters of glycerol yielding 20 liters of treatment solution, which can be used at a temperature between ambient temperature and 45° C., and preferably between 38° and 42° C., to preserve numerous varieties of plants and bushes.

I claim:

1. A dry preparation for use in dissolved form for the preservation of plants or parts thereof, containing essentially 1–6% by weight of citric acid, 30–60% by weight of at least one dye and 40–60% by weight of at least one inorganic salt formed by at least one cation selected from the group consisting of potassium, sodium, calcium, magnesium and manganese, and at least one anion selected from the group consisting of nitrate, chloride, sulfate, carbonate and phosphate.

2. The dry preparation of claim 1, in which the dye is selected from the group consisting of tartrazine, patent blue, food green, amaranth red, para-orange, quinoline yellow, sunset yellow, ponceau 4R and erythrosine.

3. The dry preparation of claim 1, in which the inorganic salt is selected from the group consisting of potassium nitrate, sodium sulfate, mixed calcium and magnesium carbonate, manganese sulfate and calcium hydrogen phosphate.

4. A solution for the preservation of the plants or parts thereof, containing a dry preparation of claim 1 in a solvent comprising water and glycerol.

5. The solution of claim 4, containing 1–3% by weight of the dry preparation.

6. The solution of claim 4, containing 25–45% by volume of glycerol and 75–55% by volume of water.

7. The solution of claim 4 for the preservation of conifer trees, containing additionally 1–2,5% by the volume of a compound selected from the group consisting of ethanol methanol.

8. A method for the preservation for plants or parts thereof, in which the roots or the lower part of the freshly cut stem of the plant is immersed in the solution of claim 4 and subsequently dried.

9. The method of claim 8, in which the immersion is carried out at an ambient humidity not exceeding 60%, for 20 hours to 10 days, the solution being maintained at a temperature between 15° C. and 45° C.

* * * * *